US009956382B2

(12) United States Patent
Hwang

(10) Patent No.: US 9,956,382 B2
(45) Date of Patent: May 1, 2018

(54) GUIDE WIRE INSERTION APPARATUS USED IN CATHETERIZATION

(75) Inventor: Sung Oh Hwang, Wonju-si (KR)

(73) Assignee: Yonsei University Wonju Industry—Academic Cooperation Foundation, Gangwon-Do (KR)

( * ) Notice: Subject to any disclaimer, the term of this patent is extended or adjusted under 35 U.S.C. 154(b) by 638 days.

(21) Appl. No.: 14/368,524

(22) PCT Filed: Dec. 29, 2011

(86) PCT No.: PCT/KR2011/010335
§ 371 (c)(1),
(2), (4) Date: Jun. 25, 2014

(87) PCT Pub. No.: WO2013/100233
PCT Pub. Date: Jul. 4, 2013

(65) Prior Publication Data
US 2015/0202414 A1 Jul. 23, 2015

(51) Int. Cl.
*A61M 25/09* (2006.01)
*A61B 5/153* (2006.01)
(Continued)

(52) U.S. Cl.
CPC ....... *A61M 25/09041* (2013.01); *A61B 5/153* (2013.01); *A61B 5/15003* (2013.01);
(Continued)

(58) Field of Classification Search
CPC ... A61M 25/09041; A61M 2025/09116; A61B 5/150236
See application file for complete search history.

(56) References Cited

U.S. PATENT DOCUMENTS

| 5,147,314 A | 9/1992 | Vaillancourt |
| 5,524,635 A | 6/1996 | Uflacker et al. |

(Continued)

FOREIGN PATENT DOCUMENTS

| EP | 2279773 | 2/2011 |
| JP | 07095983 | 4/1995 |

(Continued)

OTHER PUBLICATIONS

European Patent Office, "Supplementary European Search Report" issued in connection to International Application No. 11878529.4-1506/2799021, dated Jul. 22, 2015. 8 pages.
(Continued)

*Primary Examiner* — Daniel Cerioni
*Assistant Examiner* — Yasmeen S Warsi
(74) *Attorney, Agent, or Firm* — McKee, Voorhees & Sease, PLC

(57) ABSTRACT

Disclosed herein is a guide wire insertion device for a catheter procedure. The guide wire insertion device for a catheter procedure includes an injection unit (100) including an injection needle, and a guide wire transfer unit (200) which transfers a guide wire so as to insert the guide wire through the injection needle, and the injection unit and the guide wire transfer unit are integrated with each other so as to continuously perform injection of the injection needle and transfer of the guide wire. According to such a configuration, the injection of the injection needle and the insertion of the guide wire may be accurately and easily performed so that a catheter procedure is convenient.

5 Claims, 14 Drawing Sheets

(51) Int. Cl.
    *A61B 5/15*      (2006.01)
    *A61B 5/155*     (2006.01)
(52) U.S. Cl.
    CPC .. *A61B 5/150236* (2013.01); *A61B 5/150244*
           (2013.01); *A61B 5/150389* (2013.01); ***A61B
           5/150519*** (2013.01); *A61B 5/155* (2013.01);
                              *A61M 2025/09116* (2013.01)

(56)            References Cited

U.S. PATENT DOCUMENTS 5,690,669  A     11/1997  Sauer et al.
    6,109,264  A  *   8/2000  Sauer ............... A61M 16/0472
                                                      128/200.26
    6,217,558  B1     4/2001  Zadini et al.
    2007/0185413 A1   8/2007  Asai et al.
    2010/0087755 A1*  4/2010  Boezaart ........... A61M 25/0113
                                                      600/585

FOREIGN PATENT DOCUMENTS

JP       2010523218         7/2010
    KR     1020030001073        1/2003
    WO      2005087304 A1       9/2005
    WO       2008137956        11/2008

OTHER PUBLICATIONS

United States Patent and Trademark Office, "Certificate of Correction", Issued in connection to U.S. Pat. No. 5,147,314. 1 page.
PCT/KR2011/010335 filed Dec. 29, 2011, "The International Search Report", dated Apr. 7, 2013.

\* cited by examiner (a) (b)

GUIDE WIRE INSERTION APPARATUS USED IN CATHETERIZATION

CROSS REFERENCE TO RELATED APPLICATIONS

This is a National Phase application claiming priority to PCT/KR2011/010335 filed Dec. 29, 2011, herein incorporated by reference in its entirety.

BACKGROUND OF THE INVENTION

Field of the Invention

The present invention relates to a guide wire insertion device for a catheter procedure, and more particularly, to a guide wire insertion device for a catheter procedure, which facilitates injection of an injection needle and insertion of a guide wire during a catheter procedure.

Description of the Prior Art

A catheter is a medical cannula used to observe lesions within the human body, inject drugs, or extend a narrowed inner cavity. The catheter is used to treat diseases on various parts, and in particular is mainly used in the form of being inserted into a blood vessel such as a vein or an artery.

A central venous catheter as an example of the catheter serves as a passage through which transfusion agents or drugs are administered into the vein. In general, the central venous catheter is frequently used when it is necessary to measure venous pressure, hold the catheter in the vein for a long time, or easily administer a large amount of transfusion agents or blood preparations into the vein in a short time, during an operation or in an intensive care unit or an emergency room.

The catheter is generally inserted into the vein such as a subclavian vein, a jugular vein, a femoral vein, or a great saphenous vein. A method of inserting the catheter into, for example, the subclavian vein is performed by first inserting a relative thick syringe toward the subclavian vein, identifying that venous blood is drawn (collected) into the syringe so as to identify that an injection needle is inserted into the subclavian vein, removing the syringe in a state of leaving only the injection needle to insert a guide wire into the injection needle, removing the injection needle in a state of leaving the guide wire, inserting the catheter into the vein along the guide wire, and removing the guide wire in a state of leaving the catheter. In such a way, a method of inserting the catheter into the jugular vein or the femoral vein is also performed.

However, the conventional catheter procedure has inconvenient problems since a process for injection of the injection needle and insertion of the catheter is complex, the blood vessel may be damaged and the procedure may end in failure by removal of the injection needle from the blood vessel due to unstable operation when an operator removes the syringe, particularly in the state of leaving only the injection needle to insert the guide wire into the injection needle, and the insertion length of the guide wire may is not accurately and freely adjusted.

SUMMARY OF THE INVENTION

Therefore, the present invention has been made in view of the above problems, and it is an object of the present invention to provide a guide wire insertion device for a catheter procedure, which allows injection of an injection needle and insertion of a guide wire to be accurately and easily performed so that a catheter procedure is convenient.

Other objects and advantages of the present invention can be understood by the following description, and become apparent with reference to the embodiments of the present invention. Also, it is obvious to those skilled in the art to which the present invention pertains that the objects and advantages of the present invention can be realized by the means as claimed and combinations thereof.

In accordance with an aspect of the present invention, a guide wire insertion device for a catheter procedure includes an injection unit including an injection needle, and a guide wire transfer unit which transfers a guide wire so as to insert the guide wire through the injection needle, wherein the injection unit and the guide wire transfer unit are integrated with each other so as to continuously perform injection of the injection needle and transfer of the guide wire.

The injection unit may include a cylinder body which is disposed at one side of the injection needle, a piston which is slidably coupled within the cylinder body, and a connection tube portion which connects the cylinder body and the injection needle. The connection tube portion may be provided with a divergent tube portion having a wire passage which diverges from one side of the connection tube portion to guide the guide wire into the injection needle.

The piston may be provided, at an end thereof, with a sliding portion which slides along an upper side portion of the guide wire transfer unit according to movement of the piston, and an injection handle may be provided outside the sliding portion such that an operator injects the injection needle by easily operating the piston.

The divergent tube portion may be provided with a hemostasis valve to prevent a leakage through the wire passage during the injection of injection needle.

The guide wire transfer unit may include a housing, a driving roller which is rotatably installed within the housing to come into contact with the guide wire, a transfer roller which transfers the guide wire by rotating the guide wire in a state of pressing the guide wire against the driving roller, a driving source installed in the housing to drive the driving roller, and a transfer roller separation means which selectively separates the transfer roller from the driving roller so that the guide wire is freely transferred or prepared for transfer.

The housing may be formed with a support portion for supporting the injection unit, the support portion may be formed, at a lower side thereof, with a guide band on which guide holes for guiding the guide wire are formed in a longitudinal direction of the support portion, and the guide band may be formed with an avoidance portion of a predetermined section by which the guide holes are exposed so that the guide wire is bent and deviates from the avoidance portion when the guide wire is not transferred.

The driving source may be a spiral torsion spring coupled to the driving roller, and the housing may be equipped with a loading knob for rotation of the driving roller so as to apply torsional force to the spiral torsion spring while being equipped with a trigger so as to maintain the torsional force by catching the loading knob or to rotate the driving roller by the spiral torsion spring by releasing the caught loading knob.

A driven gear portion may be axially provided at one side of the driving roller, a driving gear engaging with the driven gear portion may be installed within the housing, the driving source may be a spiral torsion spring coupled to the driving gear, and the housing may be equipped with a loading knob for rotation of the driving roller so as to apply torsional force to the spiral torsion spring while being equipped with a trigger so as to maintain the torsional force by catching the loading knob or to rotate the driving roller by the spiral torsion spring by releasing the caught loading knob.

The driving source may be a driving motor coupled to the driving roller.

A driven gear portion may be axially provided at one side of the driving roller, a driving gear engaging with the driven gear portion may be installed within the housing, and the driving source may be installed to the driving gear.

The transfer roller separation means may include a moving plate portion which is installed to the housing and has a catching portion such that the transfer roller is rotatably fitted to one end of the moving plate portion and the moving plate portion is movable together with the transfer roller, a first elastic body installed between the housing and the moving plate portion so as to apply elastic restoring force to the moving plate portion, a holding portion which holds the catching portion to restrict movement of the moving plate portion, and a second elastic body which is installed in the housing so as to apply elastic restoring force to the holding portion.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
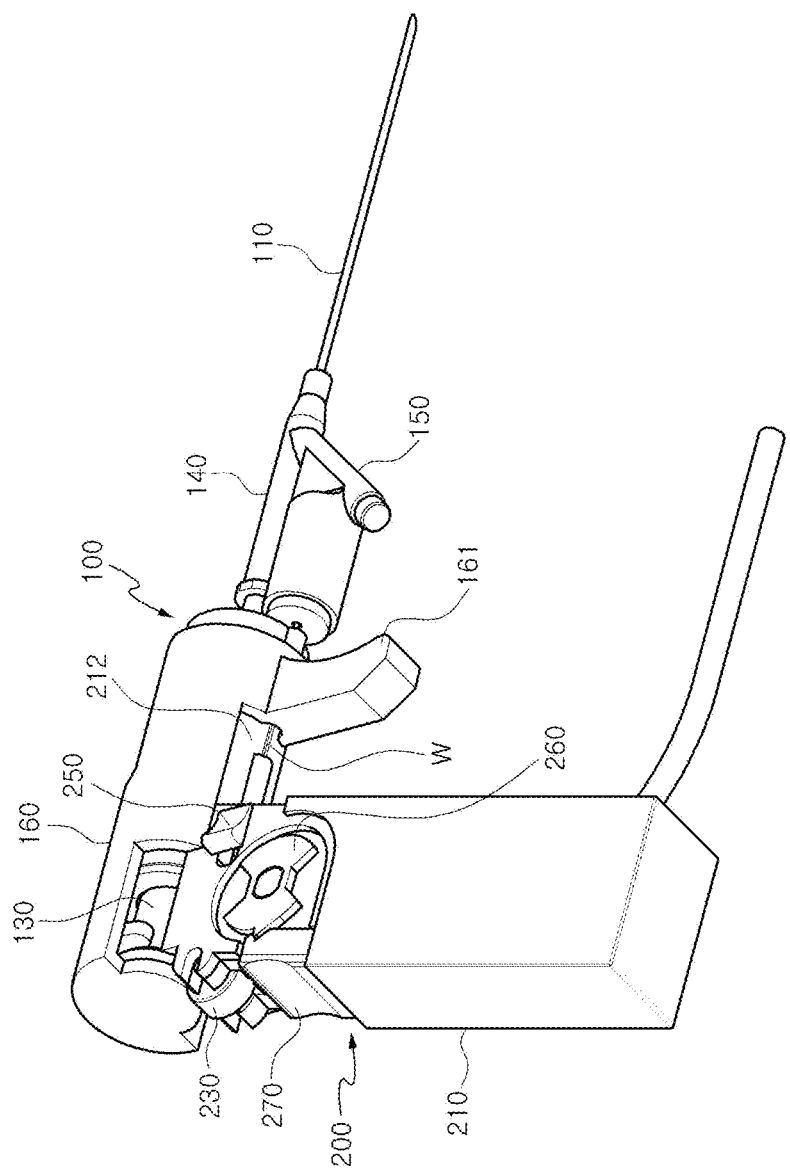
FIG. 1 an overall perspective view illustrating a guide wire insertion device for a catheter procedure according to a first embodiment of the present invention.

Reference will now be made in detail to the embodiments of the present invention, examples of which are illustrated in the accompanying drawings, wherein like reference numerals refer to like elements throughout.

Hereinafter, although a guide wire insertion device for a catheter procedure according to the present invention will be described based on an injection unit as a blood collection unit, the present invention is not limited thereto. For example, the injection unit may also be used for other purposes without departing from the spirit and scope of the present invention.

Figure 2:
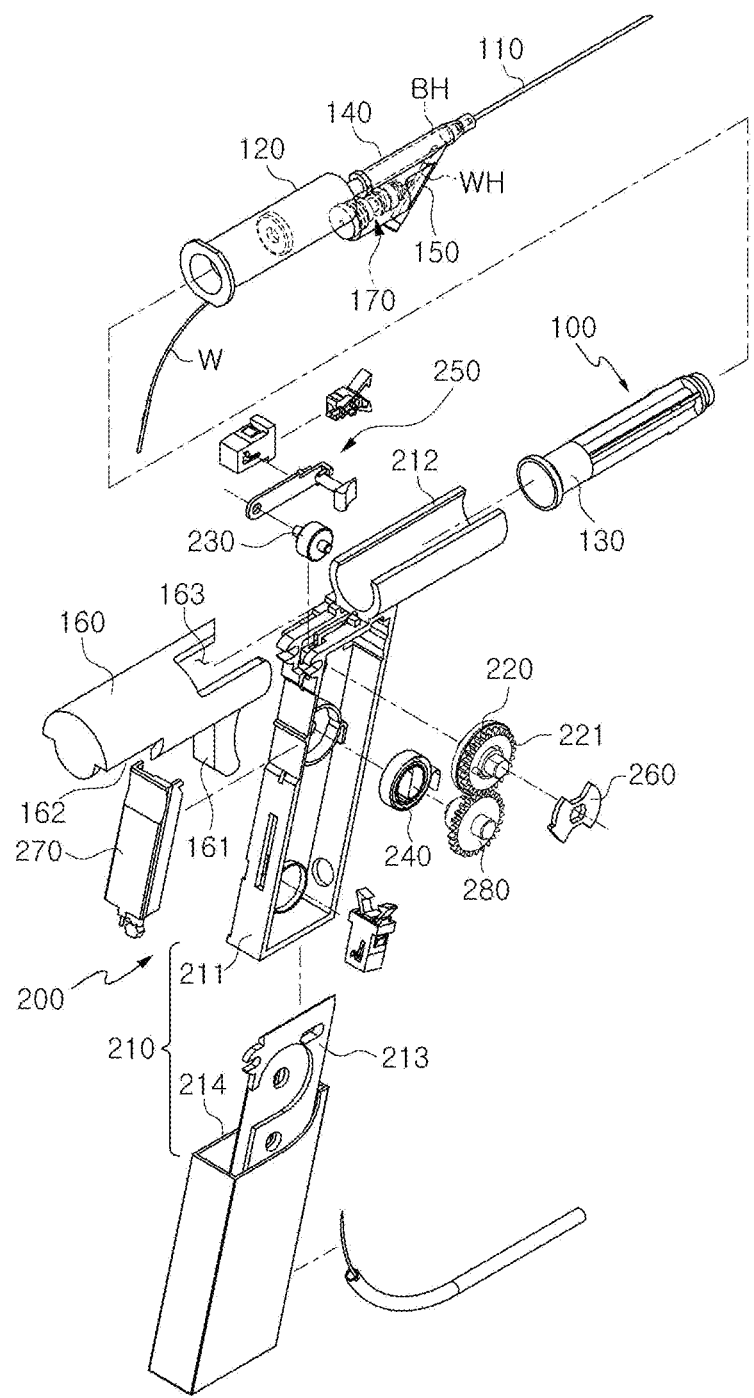
FIG. 2 is an exploded perspective view illustrating the guide wire insertion device for a catheter procedure according to the first embodiment of the present invention.

FIGS. 1 and 2 are an overall perspective view and an exploded perspective view illustrating a guide wire insertion device for a catheter procedure according to a first embodiment of the present invention. As shown in the drawings, the guide wire insertion device for a catheter procedure according to the present invention is in the form of a gun which may be generally grasped with one hand to be smoothly operated. The guide wire insertion device for a catheter procedure includes an injection unit 100 which is provided with an injection needle 110 inserted into a blood vessel to collect blood, and a guide wire transfer unit 200 which transfers a guide wire W so as to insert the guide wire W into the blood vessel through the injection needle 110. The injection unit 100 and the guide wire transfer unit 200 have a structure integrated with each other so as to continuously perform injection of the injection needle and transfer of the guide wire.

The injection unit 100 includes an injection needle 110, a cylinder body 120 which stores blood collected through the injection needle 110, a piston 130 which is slidably coupled in the cylinder body 120, and a connection tube portion 140 which connects the cylinder body 120 and the injection needle 110 and has a blood passage BH for flow of blood.

The connection tube portion 140 is provided with a divergent tube portion 150 having a wire passage WH which diverges from the blood passage BH to guide the guide wire W into the injection needle 110. A sliding portion 160, which slides along an upper side portion of the guide wire transfer unit 200 according to movement of the piston 130, is fixed to an end of the piston 130. An injection handle 161 is integrally formed outside the sliding portion 160 such that an operator collects blood by easily operating the piston 130. The divergent tube portion 150 is equipped therein with a hemostasis valve 170 to prevent a leakage of blood through the wire passage WH during blood collection.

The guide wire transfer unit 200 includes a housing 210 having a housing frame 211, a driving roller 220 which is rotatably installed within the housing 210 to come into contact with the guide wire W, a transfer roller 230 installed in the housing 210 such that the guide wire W is transferred by rotating in a state of being pressed against the driving roller 220, a spiral torsion spring (a driving source) 240 installed in the housing 210 to drive the driving roller 220, and a transfer roller separation means 250 which selectively separates the transfer roller 230 from the driving roller 220 so that the guide wire W is freely transferred or prepared for transfer.

The housing frame 211 of the housing 210 is integrally formed, at an upper side thereof, with a support portion 212 to which the cylinder body 120 of the injection unit 100 is seated and installed. A loading knob 260 for rotation of the driving roller 220 is provided outside a housing cover of the housing 210 to be described later such that the loading knob 260 is installed to a shaft of the driving roller 220 so as to apply torsional force to the spiral torsion spring 240. A trigger 270 is installed outside the housing frame 211 of the housing 210 to slide along a side surface of the housing frame 211 in a longitudinal direction thereof, so as to maintain the torsional force by catching the loading knob 260 or to rotate the driving roller 220 by the spiral torsion spring 240 by releasing the caught loading knob 260.

Figure 3:
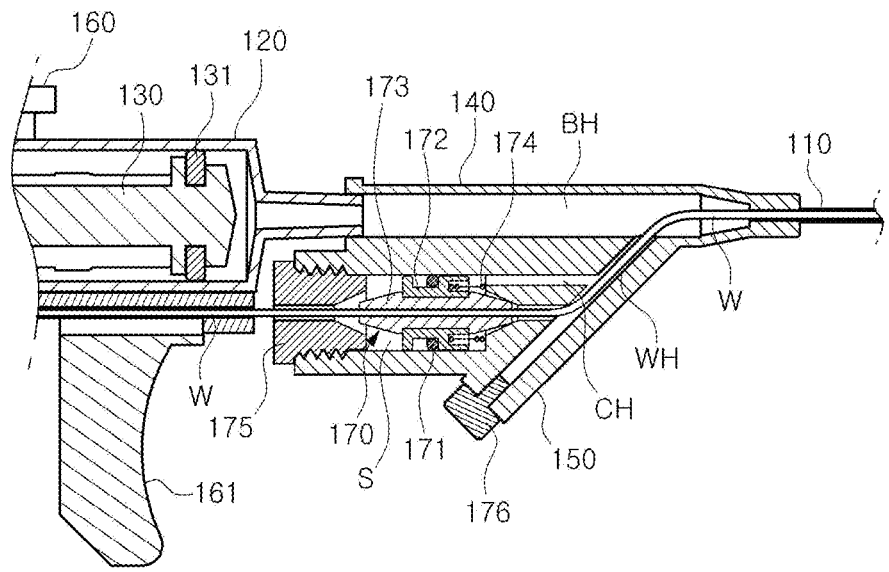
FIG. 3 is a cross-sectional view illustrating a front portion of an injection unit in FIG. 1.

FIG. 3 is a cross-sectional view illustrating a front portion of the injection unit in FIG. 1. As shown in the drawings, the injection needle 110 is formed integrally with the connection tube portion 140, a protrusion portion is formed at the front of the cylinder body 120, a rear side end of the connection tube portion 140 is fixedly fitted to the protrusion portion, and a seal member 131 for preventing a leakage of blood is fitted to a front side end of the piston 130.

The hemostasis valve 170 installed within the divergent tube portion 150 is a known valve. In the hemostasis valve 170, an elastic body 173 both ends of which are conical is inserted into a slider 172 to which an O-ring 171 is coupled, a spring 174 to apply elastic restoring force to the slider 172 is provided in a sliding space S, the sliding space S communicates with the wire passage WH through a communication hole CH, and the sliding space S and the wire passage WH are sealed by first and second cap members 175 and 176.

The elastic body 173 of the hemostasis valve 170 presses the first cap member 175 by the spring 174 together with the slider 172 during normal time to seal the sliding space S by tightening the guide wire W. During blood collection, the elastic body 173 of the hemostasis valve 170 presses the right of the sliding space S by negative pressure generated in the communication passage CH according to movement of the piston 130 to the left so as to seal the sliding space S by tightening the guide wire W, thereby preventing a leakage of blood.

The sliding portion 160 slides along an outside surface of the support portion 212 of the housing. In the sliding portion 160, a left end of the piston 130 is fixed into a left end of the sliding portion 160, a first open portion 162 to which the piston 130 is exposed is formed at a left lower portion of the sliding portion 160, a second open portion 163 to which the cylinder body 120 is exposed is formed at a right upper portion of the sliding portion 160, and a handle 161 in the form of a cover is provided at a right lower portion of the sliding portion 160.

Figure 4:
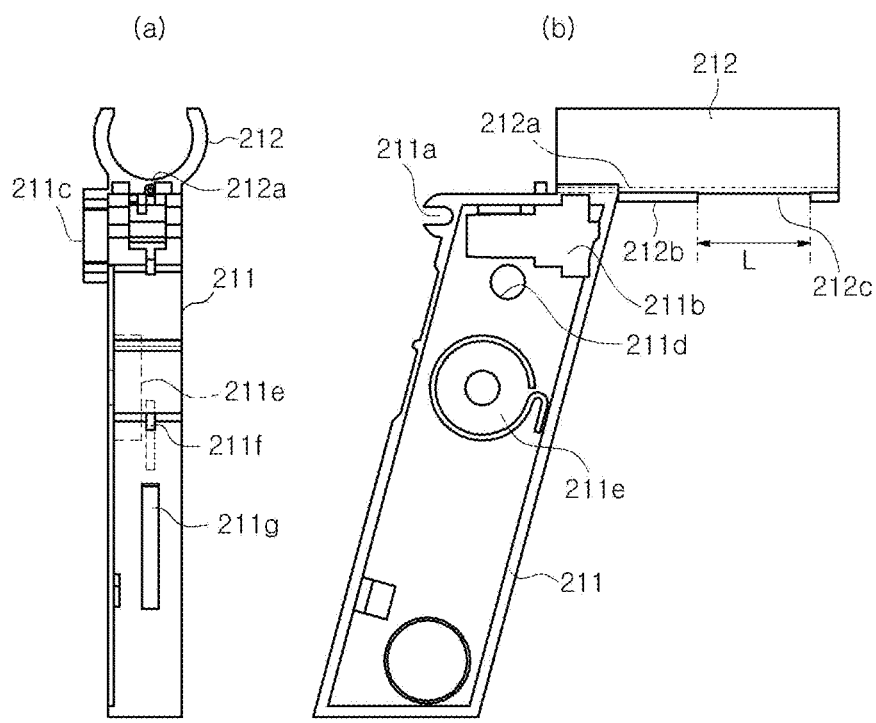
FIGS. 4(*a*) and (*b*) are a side view and an elevation view of a housing frame in FIG. 2.
Figure 5:
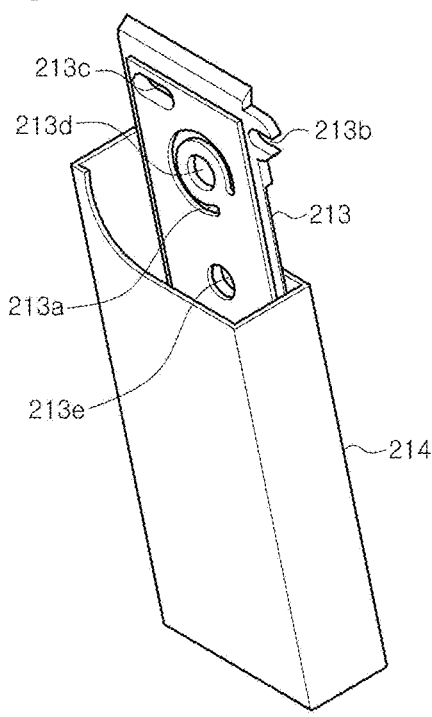
FIG. 5 is a perspective view illustrating the inside of a coupled state between a housing cover and an outer container of a housing in FIG. 2.

FIGS. 4(a) and (b) are a side view and an elevation view of the housing frame in FIG. 2. FIG. 5 is a perspective view illustrating the inside of a coupled state between a housing cover and an outer container of the housing in FIG. 2. As shown in the drawings, the housing 210 (see FIG. 2) includes a housing frame 211 formed integrally with the support portion 212 to which the cylinder body 120 is seated and installed, a housing cover 213 to cover the housing frame 211, and an outer container 214 fitted outside the housing frame 211 and the housing cover 213.

The housing frame 211 is formed therein with a receiving portion and has a rectangular container shape opened at one side thereof. In the housing frame 211, a groove portion 211a into which a shaft of the transfer roller 230 is inserted is formed at an upper side edge of the housing frame 211, a protrusion portion 211c which outwardly protrudes is formed at an upper portion of the housing frame 211 so as to be formed therein with a receiving portion 211b into which a holding portion of the transfer roller separation means 250 to be described later is inserted, a hole 211d into which the shaft of the driving roller 220 is inserted to install the driving roller 220 is formed beneath the receiving portion 211b, a spring installation portion 211e into which the spiral torsion spring 240 is inserted is formed beneath the hole 211d, and the side surface of the housing frame 211 is formed with a hole 211f through which the guide wire W passes while being formed with a sliding slot 211g into which a catching portion of the trigger 270 to be described later is slidably inserted.

The support portion 212 has a container shape opened at an upper side thereof. The support portion 212 is formed, at a lower side thereof, with a guide band 212b on which guide holes 212a for guiding the guide wire W are formed along the support portion 212 in a longitudinal direction thereof. The guide band 212b is formed with an avoidance portion 212c of a predetermined section L in which the guide holes 212a are partially exposed to the outside so that the guide wire W is bent and deviates through the avoidance portion 212c when the guide wire W is not transferred.

Figure 6:
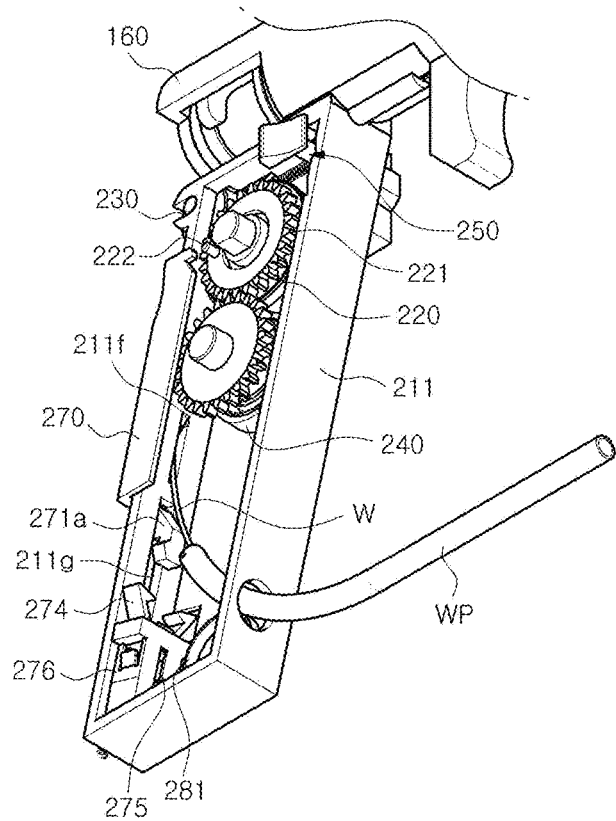
FIG. 6 is a perspective view illustrating a state in which components are assembled in the housing frame in FIG. 2.

FIG. 6 shows that the housing frame 211 is equipped therein with the driving roller 220, the driving gear to be described later, the transfer roller 230, the spiral torsion spring 240, the transfer roller separation means 250, the trigger 270, a catching portion 271a, a holding portion 274, and a holder container 276 of the trigger 270 to be described later, and a guide portion 281 which guides a protective tube WP for protection of the guide wire W.

The housing cover 213 is a cover to cover an opening portion of the housing frame 211. In the housing cover 213, an inner surface of the housing cover 213 is formed with a guide groove 213a forming a circular arc band so that a protrusion of the driving roller 220 to be described later is guided to the guide groove 213a so as to transfer the guide wire W by a length of a circular arc, an upper side edge of the housing cover 213 is formed with a groove portion 213b into which the shaft of the transfer roller 230 is inserted, an upper portion of the housing cover 213 is formed with a sliding slot 213c into which a knob shaft of the transfer roller separation means 250 to be described later is slidably inserted, a center of the guide groove 213a is formed with a hole 213d into which the shaft of the driving roller 220 is inserted to install the driving roller 220, and a hole 213e to which the driving gear to be described later is installed is formed beneath the hole 213d.

As shown in FIG. 6, a driven gear portion 221 is axially formed at one side of the driving roller 220, a driving gear 280 engaging with the driven gear portion 221 is installed within the housing frame 211 of the housing 210, the spiral torsion spring 240 is installed to the spring installation portion 211e to drive the driving gear 280. According to a structure having the driving gear 280, transfer speed of the guide wire may be controlled by an increase or decrease in speed. The driving roller 220 is formed with a protrusion 222 which is fitted into and guided by the guide groove 213a.

Meanwhile, the spiral torsion spring 240 may be directly installed to the driving roller 220 regardless of the driven gear portion 221 and the driving gear 280, thereby enabling the driving roller 200 to be also driven.

As shown in FIG. 1, the transfer roller 230 is provided to be exposed outward of the housing 210 so as to transfer the guide wire W coming into contact with the driving roller 220 by rotating the transfer roller 230 with a user' hand.

Figure 7:
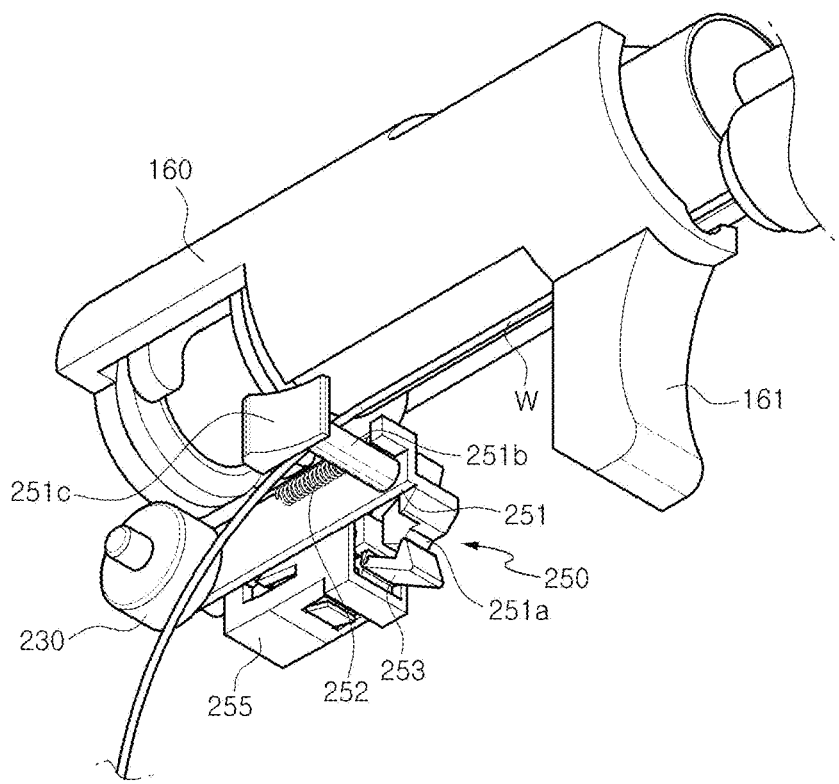
FIG. 7 is a view illustrating an assembled state of a transfer roller separation means in FIG. 2.
Figure 8:
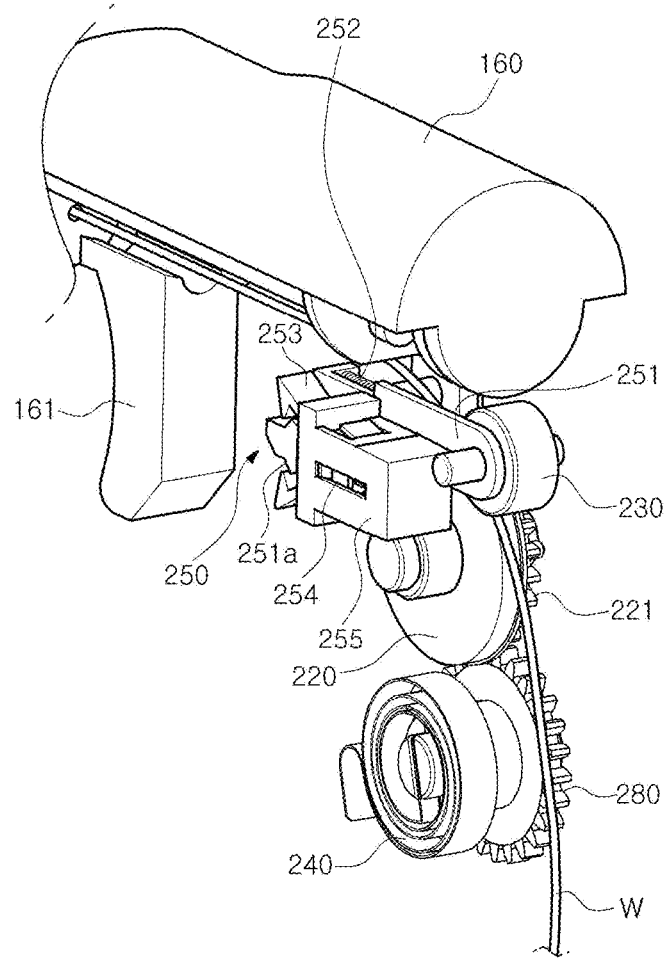
FIG. 8 is a perspective view when viewed from the right in FIG. 7, a driving roller, a driving gear, and a spiral torsion spring being shown together in FIG. 8.

FIG. 7 is a view illustrating an assembled state of the transfer roller separation means in FIG. 2. FIG. 8 is a perspective view when viewed from the right in FIG. 7, and the driving roller, the driving gear, and the spiral torsion spring are shown together in FIG. 8. As shown in the drawings, the transfer roller separation means 250 includes a moving plate portion 251 which is installed to the housing 210 and has a catching portion 251a so that the transfer roller 230 is rotatably fitted to one end of the moving plate portion 251 and the moving plate portion 251 is movable together with the transfer roller 230, a first elastic body (a coil spring) 252 installed between the housing 210 and the moving plate portion 251 so as to apply elastic restoring force to the moving plate portion 251, a holding portion 253 which holds the catching portion 251*a* to restrict movement of the moving plate portion 251, and a second elastic body (a spring) 254 to apply elastic restoring force to the holding portion 253.

A knob shaft 251*b* inserted into the sliding slot 213*c* of the sousing cover 213 protrudes from an end opposite to the side of the moving plate portion 251 to which the transfer roller 230 is fitted, and an end of the knob shaft 251*b* is formed with a knob 251*c* exposed outward of the housing cover 213 so that a user operates the knob 251*c*. The catching portion 251*a* protrudes from an opposite side of the knob shaft 251*b* (from a back surface of the moving plate portion).

The first elastic body (coil spring) 252 is caught, at one end thereof, by the moving plate portion 251 and the other end thereof is caught by a protrusion portion (not shown) of the housing 210.

The holding portion 253 is in the form of a hook by which both sides of the catching portion 251*a* are caught and operates about a hinge shaft which is not shown. The holding portion 253 is inserted and installed into a holder container 255 and the holder container 255 is inserted and installed into the receiving portion 211*b* (see FIG. 4) of the housing frame 211. The second elastic body 254 is inserted into the holder container 255 to operate the holding portion 253. The holding portion 253 and the second elastic body 254 may also be installed within the housing frame 211 without provision of the holder container 255 so as to operate the holding portion 253.

Figure 9:
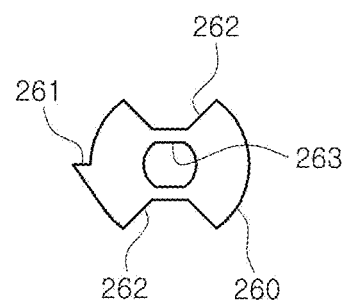
FIG. 9 is an elevation view illustrating a loading knob in FIG. 2.

As shown in FIG. 9, the loading knob 260 has a disc shape including a catching hook 261 formed on an outer peripheral surface thereof so as to be caught by a catching groove of the trigger 270 to be described later, a recessed portion 262 formed on the outer peripheral surface thereof so as to be easily rotated by a user's fingers, and a fixed hole 263 which is fitted to the shaft 223 of the driving roller 220. As shown in FIG. 1, the loading knob 260 is installed to be exposed outward of the housing 210 such that a user operates the loading knob 260.

Figure 10:
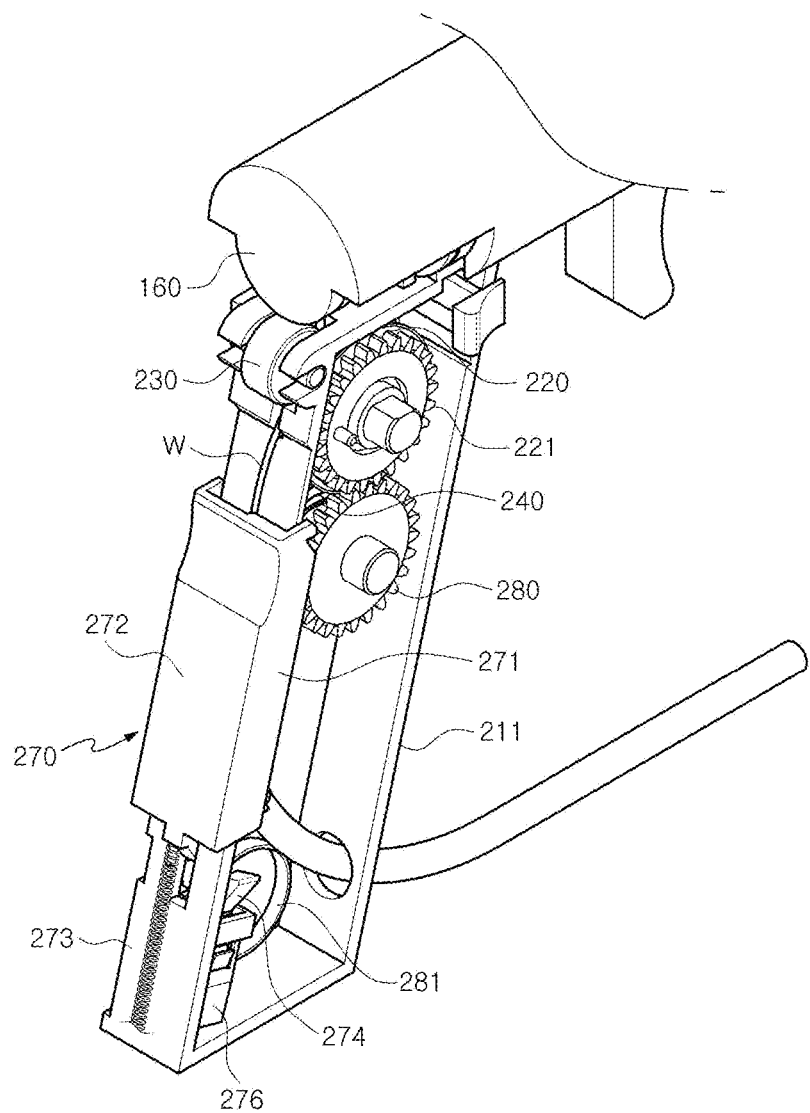
FIG. 10 is a perspective view when viewed from the left in FIG. 6.

FIG. 10 is a perspective view when viewed from the left in FIG. 6. As shown in FIGS. 6 and 10, the trigger 270 includes a trigger body 271 which is slidably fitted on the side surface of the housing frame 211 in the longitudinal direction thereof and has a catching portion 271*a* passing through the hole 211*g* and protruding inward of the housing frame 211, a trigger cover 272 which is coupled to the trigger body 271 so as to cover and guide the guide wire W drawn outward from the inside the housing frame 211 via the hole 211*f*, and a third elastic body (a coil spring) 273 installed outside the housing frame 211 so as to apply elastic restoring force to the trigger body 271 and the trigger cover 272.

The housing frame 211 is equipped therein with a holding portion 274 which holds the catching portion 271*a* to restrict movement of the trigger body 271, and a fourth elastic body (a coil spring) 275 to apply elastic restoring force to the holding portion 274. The holding portion 274 is inserted and installed into a holder container 276.

Since the catching portion 271*a*, the holding portion 274, the fourth elastic body 275, and the holder container 276 are similar to the catching portion, the holding portion, the second elastic body, and the holder container of the transfer roller separation means 250, no detailed description will be given thereof.

The guide wire W is released from a roller (not shown) to be guided into the housing frame 211 via the inside the protective tube WP. The guide portion 281 is installed at an inner lower side of the housing frame 211 and has a ring shape to support the protective tube WP.

Figure 11:
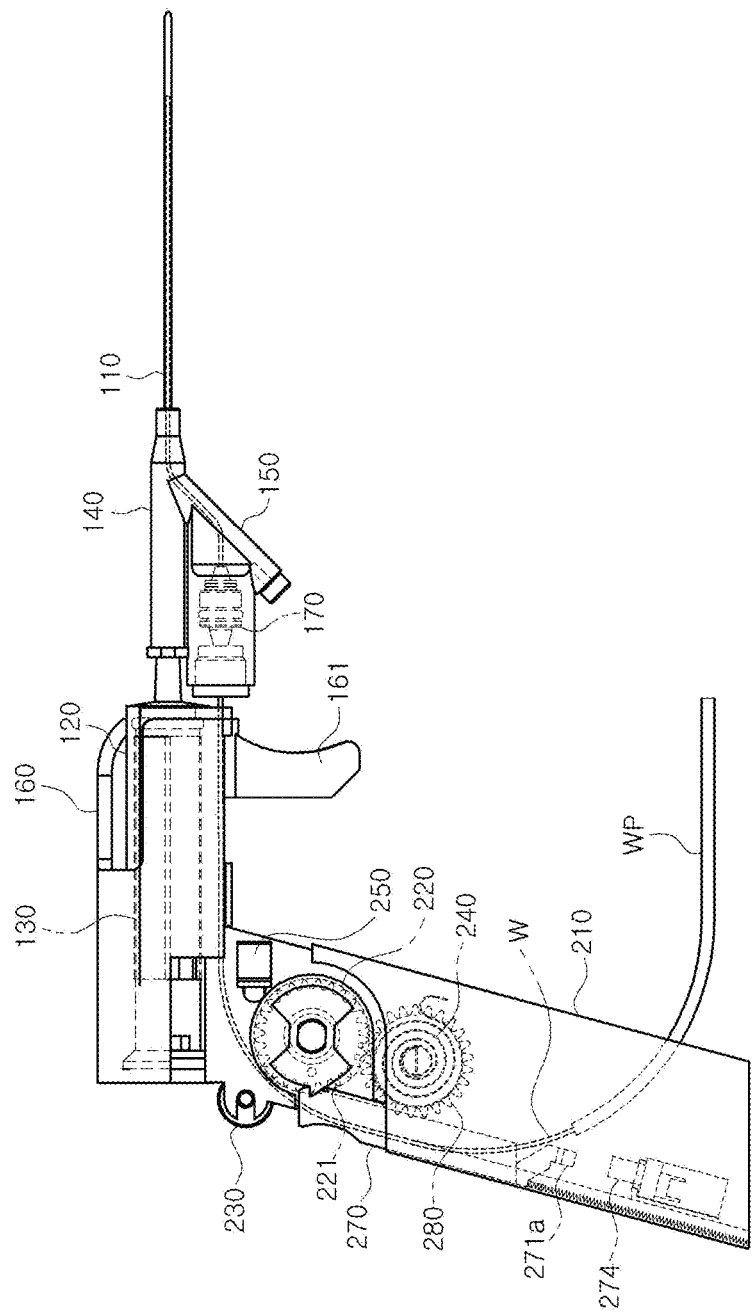
FIGS. 11 to 15 are views illustrating an operation state of the guide wire insertion device for a catheter procedure according to the first embodiment of the present invention.
Figure 12:
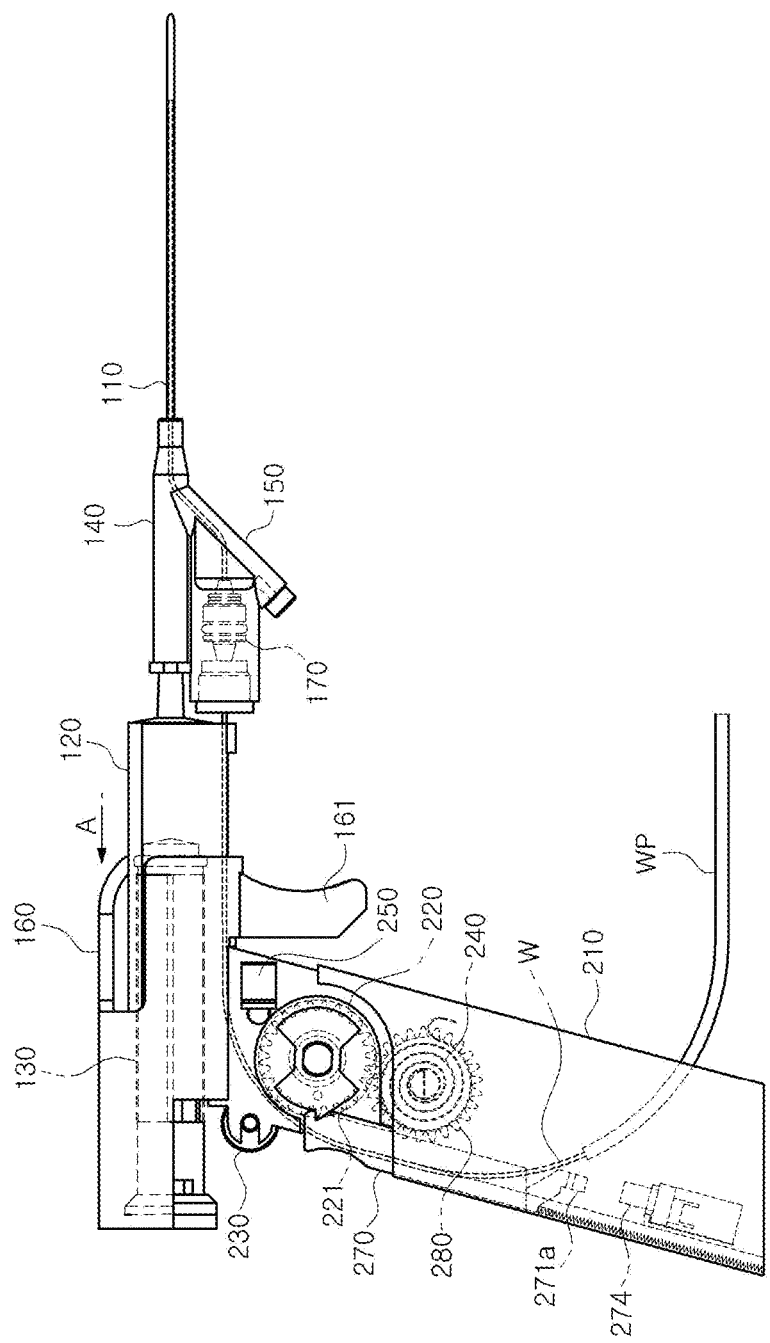

In the guide wire insertion device for a catheter procedure according to the first embodiment of the present invention having such a configuration, as shown in FIG. 11, the guide wire W inserted into the protective tube WP passes between the driving roller 220 and the transfer roller 230 along the trigger 270 to reach the inside of the injection needle 110 via the guide hole 212*a* (see FIG. 4) of the support portion 212 of the housing 221 and the hemostasis valve 170, the end of the injection needle 110 is inserted into a patient's vein, and then the handle 161 of the sliding portion 160 of the injection unit 100 is pulled in a direction of an arrow A as shown in FIG. 12. Consequently, blood is drawn (collected) into the cylinder body 120 from the patient's vein by operation of the piston 130. In this case, elastic force is applied to the spiral torsion spring 240 of the guide wire transfer unit 200 so that the loading knob 260 is in a state of being caught by the trigger 270.

Figure 13:
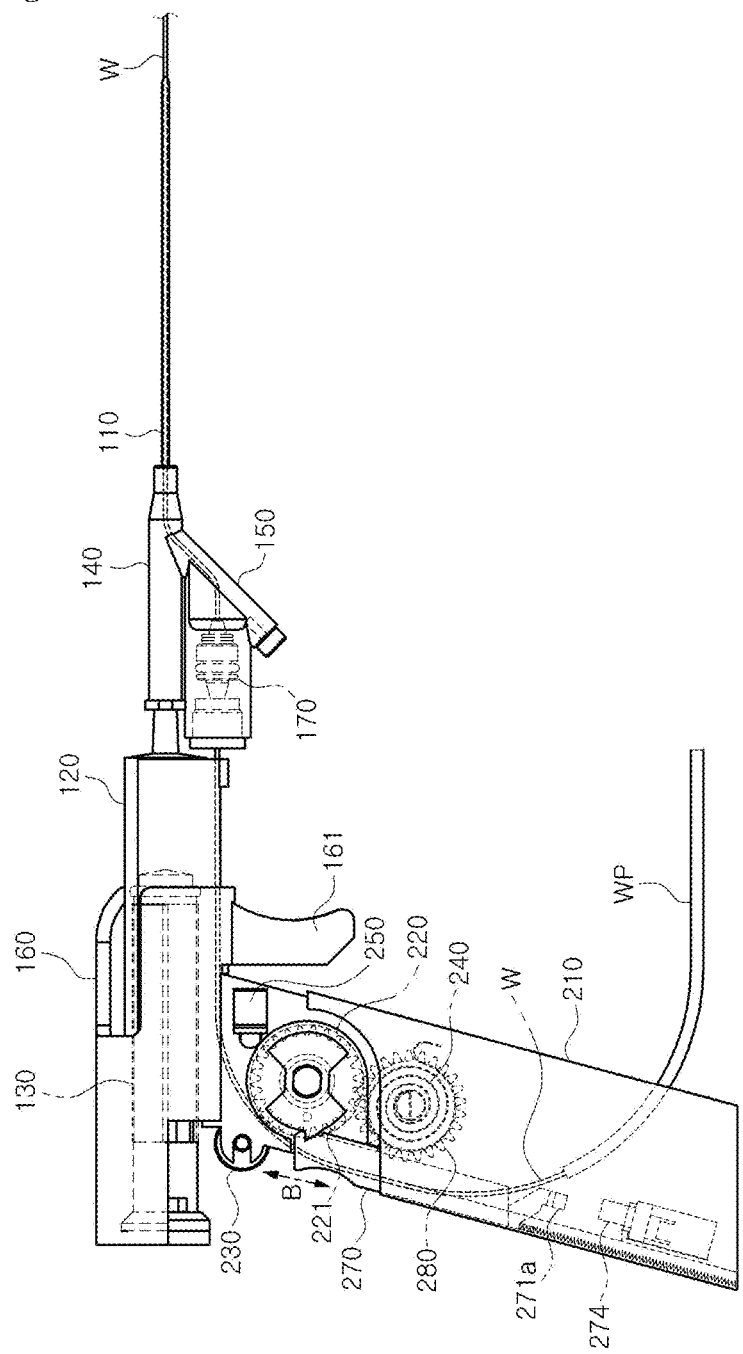

When the blood collection is identified and then the trigger 270 is slightly lifted and then dropped in a direction of an arrow B as shown in FIG. 13, the caught loading knob 260 is released and the driving roller 220 rotates in a clockwise direction so that the guide wire W fitted between the driving roller 220 and the transfer roller 230 is transferred. In this case, the protrusion 222 (see FIG. 6) coupled to the driving roller 220 is guided along the guide groove 213*a* (see FIG. 5) formed on the inner surface of the housing cover 213 so that the guide wire W is transferred only by a fixed length (a length of the guide groove).

Figure 14:
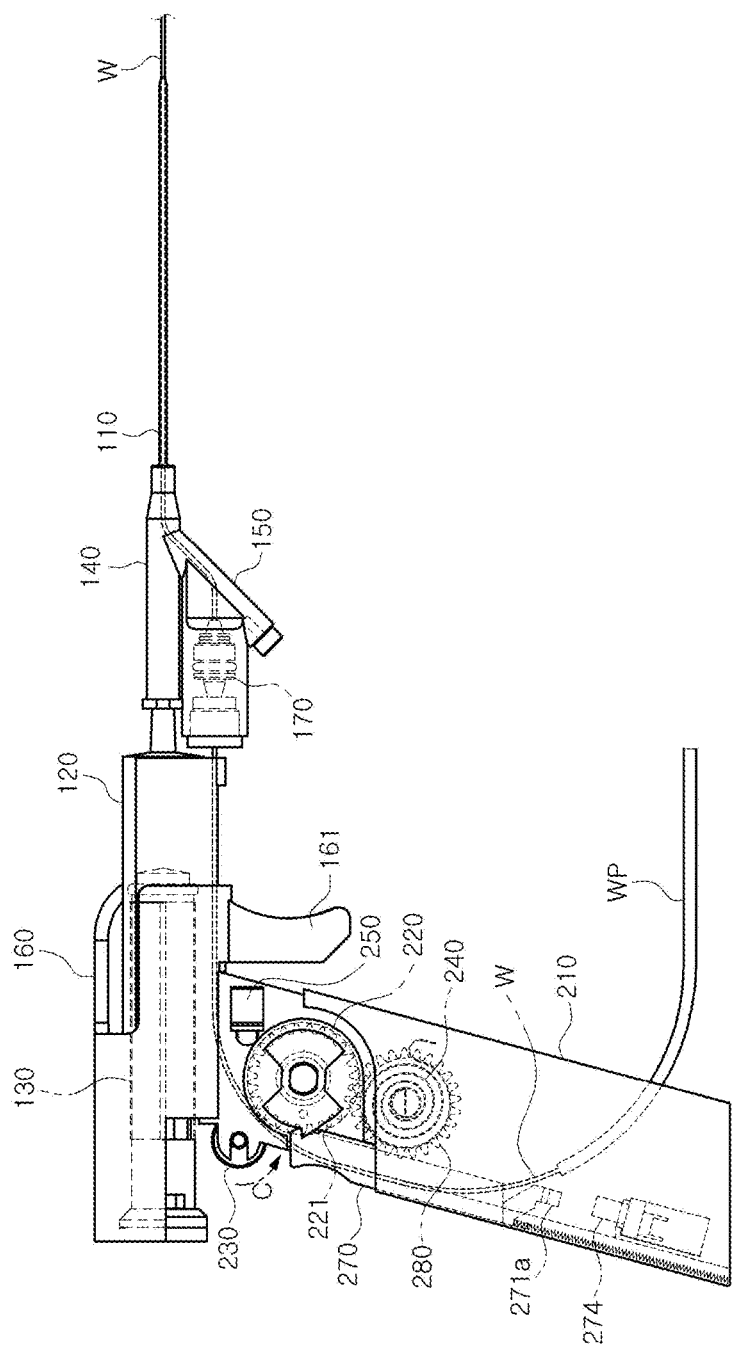

Meanwhile, in this state, when the transfer roller 230 is rotated with the hand (in a direction of an arrow C) as shown in FIG. 14, the guide wire W is minutely transferred so that a transfer distance thereof may be adjusted.

Figure 15:
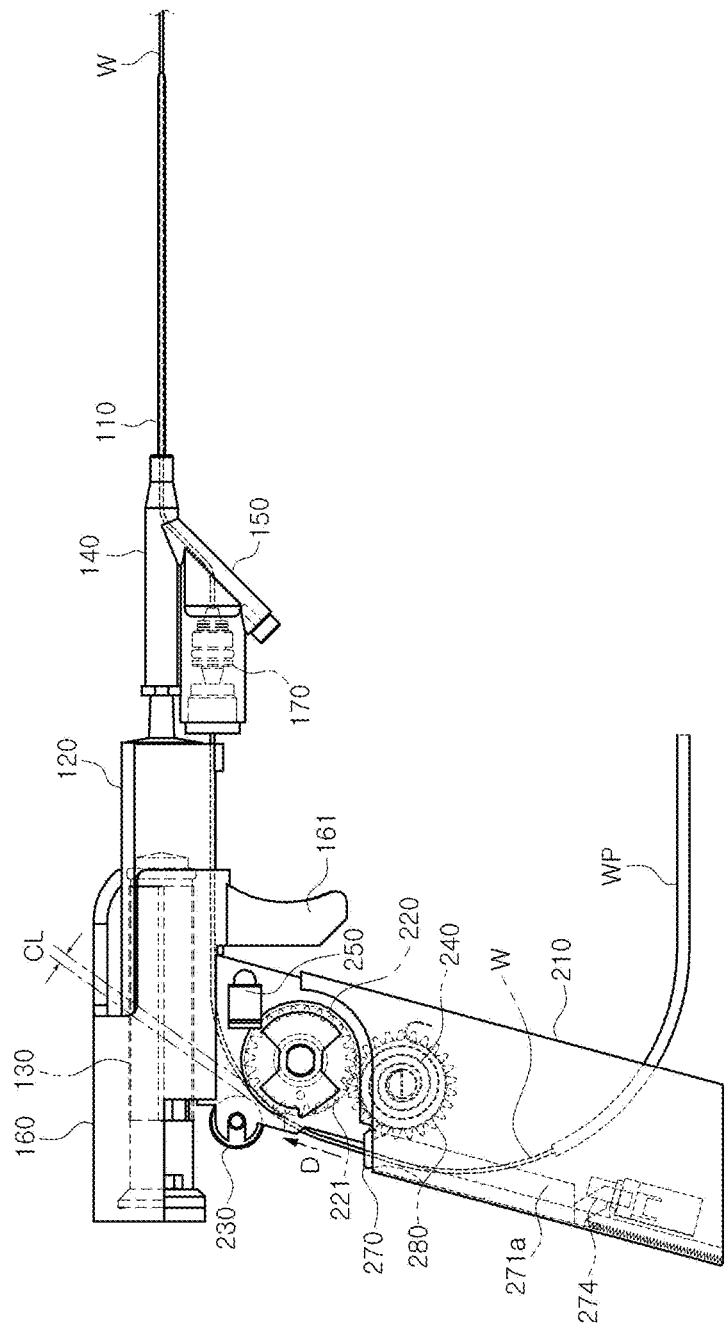

In a case where the guide wire W is intended to be freely transferred with the hand (in a direction of an arrow D), since the transfer roller 230 is maintained in a state of being spaced apart from the driving roller 220 at a predetermine interval CL when the knob 251*c* of the transfer roller separation means 250 (see FIGS. 7 and 8) is pulled rearward and the catching portion 251*a* thereof is caught by the holding portion 253 as shown in FIG. 15, the guide wire W may be freely transferred.

Figure 16:
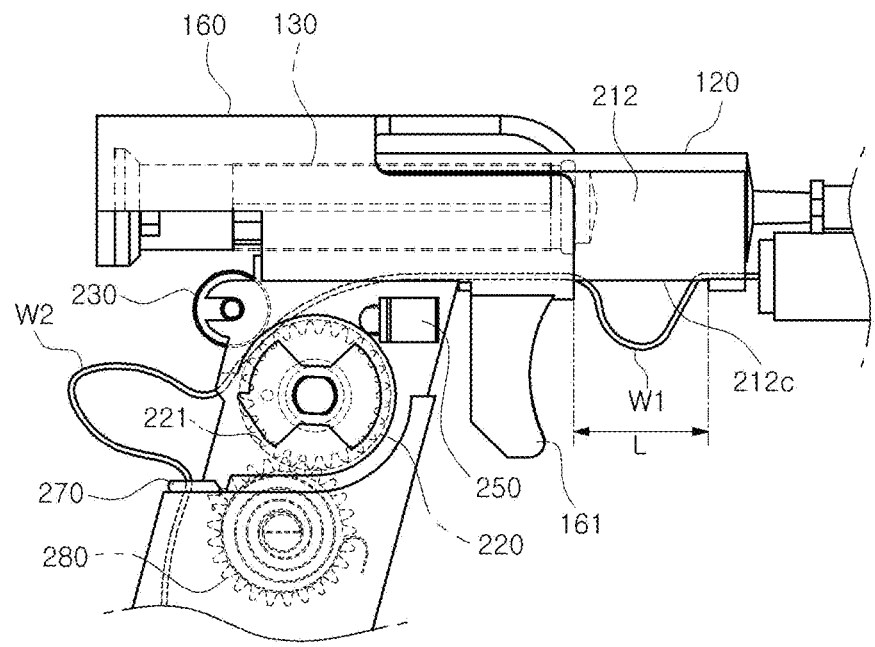
FIG. 16 is a view illustrating an operation state of a guide wire according to the first embodiment of the present invention when the guide wire fails to be transferred.

Meanwhile, in a case where the transfer of the guide wire W ends in failure, since the guide wire W is bent (indicated by W1) and deviates by being exposed to the outside by the avoidance portion 212*c* of the predetermined section L formed at the lower side portion of the support portion 212 as shown in FIG. 16, the guide wire W is not transferred any more.

Since the exposed portion of the guide wire W is also present at the upper side portion of the trigger 270, the guide wire W is exposed to the outside and is bent (indicated by W2) so as to be not transferred any more. In this case, since the transfer roller 230 is supported by the first elastic body (coil spring) 252 of the transfer roller separation means 250, the guide wire W slides to be not transferred when predetermined or more force is applied to the guide wire W.

When the guide wire W is retransferred due to failure of transfer, the loading knob 260 is rotated in a counterclockwise direction and is caught by the trigger 270 so as to be reloaded.

Figure 17:
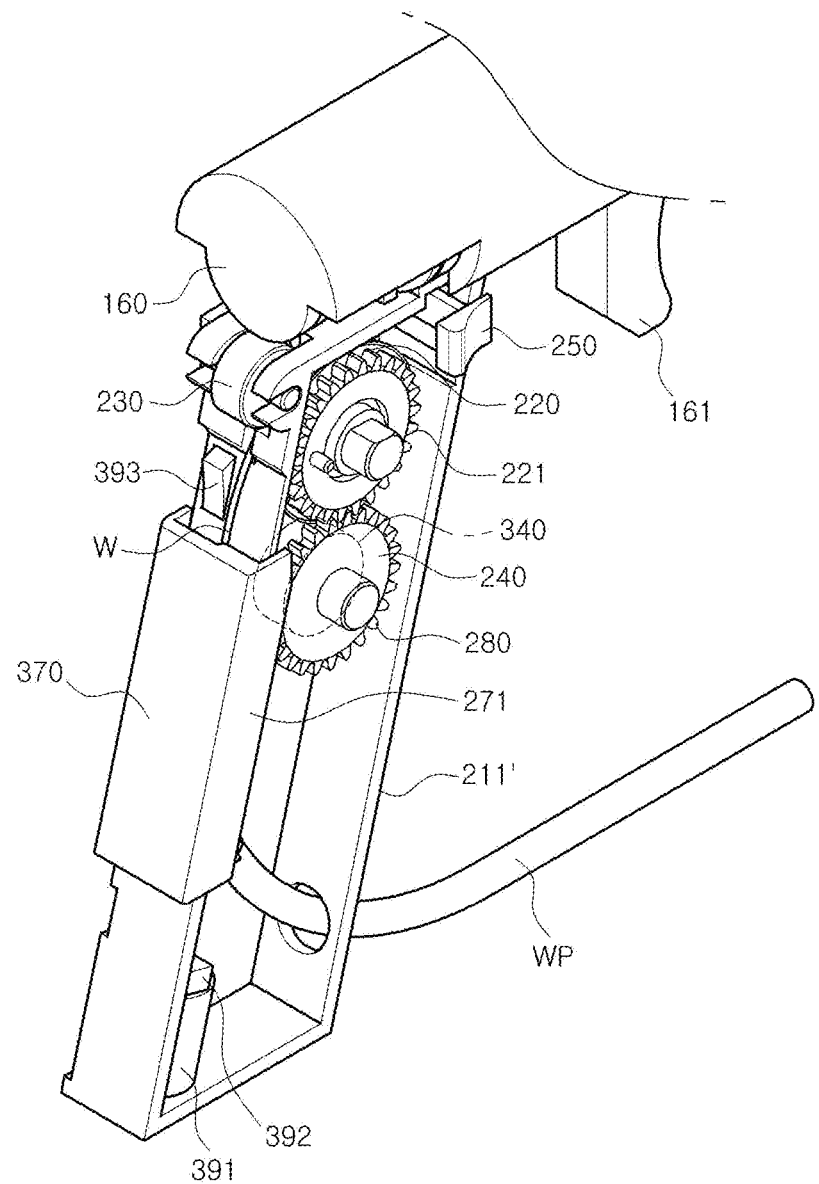
FIG. 17 is a view illustrating a configuration of a guide wire insertion device for a catheter procedure according to a second embodiment of the present invention.

FIG. 17 is a view illustrating a configuration of a guide wire insertion device for a catheter procedure according to a second embodiment of the present invention. The present embodiment (second embodiment) has a structure in which the spiral torsion spring 240 (first embodiment) as a driving source is replaced with a motor 340. A battery 391 and a control unit 392 are installed within a housing frame 211'. An outer side surface of the housing frame 211' is equipped with a switch 393 for driving the motor 340 while being equipped with a guide portion 370 for guiding the guide wire W.

Since the transfer of the guide wire is controlled by the motor 340 and the control unit 392 in the second embodiment, the loading knob 260, the trigger 270, the third elastic body 273, the holding portion 274, the fourth elastic body 275, and the holder container 276 in the first embodiment are not required.

Even in the second embodiment, the motor 340 may be directly installed to the driving roller 220 regardless of the driven gear portion 221 and the driving gear 280, thereby enabling the driving roller 200 to be also driven.

Since the remaining configurations of the second embodiment are similar to those of the first embodiment, no detailed description will be given thereof.

As is apparent from the above description, in accordance with a guide wire insertion device for a catheter procedure according to the present invention, injection of an injection needle and insertion of a guide wire may be accurately and easily performed so that a catheter procedure is convenient.

That is, the guide wire insertion device for a catheter procedure has an effect capable of continuously performing the injection of the injection needle and the transfer of the guide wire without a separate action during insertion of the catheter. It may be possible to operate an injection means (syringe) with one hand without using both hands, to transfer the guide wire by a certain length by single operation, to minutely adjust the transfer length of the guide wire, to freely transfer the guide wire, to regulate the transfer speed of the guide wire, and to safely perform the catheter operation by enabling the guide wire to be not transferred any more when the transfer thereof ends in failure.

Although the present invention has been described with respect to the illustrative embodiments, it will be apparent to those skilled in the art that various variations and modifications may be made without departing from the spirit and scope of the invention as defined in the following claims.

What is claimed is:

1. A guide wire insertion device for a catheter procedure, comprising:
   an injection unit comprising an injection needle, a cylinder body which is disposed at one side of the injection needle, a piston which is slidably coupled within the cylinder body, and a connection tube portion which connects the cylinder body and the injection needle; and
   a guide wire transfer unit, having an upper side and a lower side opposite from the upper side, which transfers a guide wire so as to insert the guide wire through the injection needle of the injection unit and comprises a housing formed with a support portion for supporting the injection unit,
   wherein the support portion supports the injection unit such that the injection unit is located at the upper side of the guide wire transfer unit so that the injection unit and the guide wire transfer unit are integrated with each other in the form of a hand gun with the guide wire transfer unit adapted to be grasped as a handle by an operator so as to continuously perform injection of the injection needle and transfer of the guide wire with one hand;
   wherein the piston is provided, at an end thereof, with a sliding portion which slides along the upper side portion of the guide wire transfer unit according to movement of the piston: and
   wherein an injection handle is provided outside and offset from the sliding portion located such that the operator collects blood through the injection needle with the one hand by adjusting the injection handle and thereby the sliding portion and piston while grasping the guide wire transfer unit and controlling transfer of the guide wire with the one hand,
   wherein the guide wire transfer unit comprises:
   a driving roll which is rotatably installed within the housing to come into contact with the guide wire:
   a transfer roller which transfers the guide wire by rotating the guide wire in a state of pressing the guide wire against the driving roller:
   a driving source installed in the housing to drive the driving roller; and
   a transfer roller separation means which selectively separates the transfer roller from the driving roller so that the guide wire is freely transferred or prepared for transfer; and
   further wherein:
   the driving source is a spiral torsion spring coupled to the driving roller; and
   the housing is equipped with a loading knob for rotation of the driving roller so as to apply torsional force to the spiral torsion spring while being equipped with a trigger so as to maintain the torsional force by catching the loading knob or to rotate the driving roller by the spiral torsion spring by releasing the caught loading knob.

2. The guide wire insertion device according to claim 1, wherein the connection tube portion of the injection unit is provided with a divergent tube portion having a wire passage which diverges from one side of the connection tube portion to guide the guide wire into the injection needle.

3. The guide wire insertion device according to claim 1, wherein:
   the support portion is formed, at a lower side thereof, with a guide band on which guide holes for guiding the guide wire are formed in a longitudinal direction of the support portion; and
   the guide band is formed with an avoidance portion by which the guide holes are exposed so that the guide wire is bent and deviates from the avoidance portion when the guide wire is not transferred.

4. A guide wire insertion device for a catheter procedure, comprising:
   an injection unit comprising an injection needle, a cylinder body which is disposed at one side of the injection needle, a piston which is slidably coupled within the cylinder body, and a connection tube portion which connects the cylinder body and the injection needle; and
   a guide wire transfer unit, having an upper side and a lower side opposite from the upper side, which transfers a guide wire so as to insert the guide wire through the injection needle of the injection unit and comprises a housing formed with a support portion for supporting the injection unit,
   wherein the support portion supports the injection unit such that the injection unit is located at the upper side of the guide wire transfer unit so that the injection unit and the guide wire transfer unit are integrated with each other in the form of a hand gun with the guide wire transfer unit adapted to be grasped as a handle by an operator so as to continuously perform injection of the injection needle and transfer of the guide wire with one hand;

wherein the piston is provided, at an end thereof, with a sliding portion which slides along the upper side portion of the guide wire transfer unit according to movement of the piston: and wherein an injection handle is provided outside and offset from the sliding portion located such that the operator collects blood through the injection needle with the one hand by adjusting the injection handle and thereby the sliding portion and piston while grasping the guide wire transfer unit and controlling transfer of the guide wire with the one hand, wherein the guide wire transfer unit comprises:

a driving roller which is rotatably installed within the housing to come into contact with the guide wire:

a transfer roller which transfers the guide wire by rotating the guide wire in a state of pressing the guide wire against the driving roller:

a driving source installed in the housing to drive the driving roller; and a transfer roller separation means which selectively separates the transfer roller from the driving roller so that the guide wire is freely transferred or prepared for transfer, wherein:

a driven gear portion is axially provided at one side of the driving roller, and a driving gear engaging with the driven gear portion is installed within the housing;

the driving source is a spiral torsion spring coupled to the driving gear; and the housing is equipped with a loading knob for rotation of the driving roller so as to apply torsional force to the spiral torsion spring while being equipped with a trigger so as to maintain the torsional force by catching the loading knob or to rotate the driving roller by the spiral torsion spring by releasing the caught loading knob.

5. The guide wire insertion device according to claim 1, wherein the transfer roller separation means comprises:

a moving plate portion which is installed to the housing and has a catching portion such that the transfer roller is rotatably fitted to one end of the moving plate portion and the moving plate portion is movable together with the transfer roller, a first elastic body installed between the housing and the moving plate portion so as to apply elastic restoring force to the moving plate portion;

a holding portion which holds the catching portion to restrict movement of the moving plate portion; and a second elastic body which is installed in the housing so as to apply elastic restoring force to the holding portion.

* * * * *